United States Patent
Yu

(10) Patent No.: US 7,488,706 B2
(45) Date of Patent: Feb. 10, 2009

(54) ALKYLAMINE AS AN ANTIMICROBIAL AGENT IN OPHTHALMIC COMPOSITIONS

(75) Inventor: Zhi-Jian Yu, Irvine, CA (US)

(73) Assignee: Advanced Medical Optics, Inc., Santa Ana, CA (US)

(*) Notice: Subject to any disclaimer, the term of this patent is extended or adjusted under 35 U.S.C. 154(b) by 246 days.

(21) Appl. No.: 11/534,990

(22) Filed: Sep. 25, 2006

(65) Prior Publication Data

US 2008/0125494 A1 May 29, 2008

Related U.S. Application Data

(62) Division of application No. 10/820,354, filed on Apr. 7, 2004, now Pat. No. 7,157,412.

(51) Int. Cl.
*C11D 1/72* (2006.01)
*C11D 1/722* (2006.01)
*C11D 3/26* (2006.01)
*C11D 3/48* (2006.01)

(52) U.S. Cl. .............. 510/112; 510/383; 510/384; 510/391; 510/506; 510/499; 510/504; 514/839; 514/840

(58) Field of Classification Search ........... 510/112, 510/383, 384, 391, 499, 504, 506; 514/839, 514/840
See application file for complete search history.

(56) References Cited

FOREIGN PATENT DOCUMENTS

WO WO2004/058930 * 7/2004

* cited by examiner

*Primary Examiner*—Gregory R Del Cotto
(74) *Attorney, Agent, or Firm*—Advanced Medical Optics Inc.

(57) ABSTRACT

A multi-purpose contact lens care solution having high activity against fungi and certain bacteria comprising, in liquid aqueous medium, an alkylamine having the following formula,

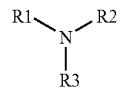

where R1 is a $C_{13-17}$ alkyl, and R2 and R3 are each independently H or $—CH_3$, and a non-ionic surfactant. The solution may optionally also include additional antimicrobial components, a buffer component, a viscosity inducing component, a surfactant, taurine, propylene glycol and/or a tonicity component. This solution additionally prevents losses in ocular tissue membrane integrity during contact lens wear.

10 Claims, No Drawings

ALKYLAMINE AS AN ANTIMICROBIAL AGENT IN OPHTHALMIC COMPOSITIONS

RELATED APPLICATIONS

This application is a divisional of allowed application Ser. No. 10/820,354 filed on Apr. 7, 2004 now U.S. Pat. No. 7,157,412.

BACKGROUND OF THE INVENTION

1. Area of the Art

The present invention relates to compositions and methods for eye and contact lens care. More particularly, the invention relates to ophthalmic compositions which contain an alkylamine as a decontaminating agent for preservation of the solution and/or disinfecting contact lenses.

2. Description of the Prior Art

Contact lens wear induces adverse changes in ocular tissues and the tear film. These changes include cornea lactic acidosis and subsequent cornea swelling as a consequence of hypoxia induced by low oxygen gas transmission, changes in corneal epithelial tissue thickness, changes in corneal epithelial and endothelial cell morphology, epithelial surface cell exfoliation, hyperemia (red eye), adverse changes in corneal and conjunctival cell membrane integrity and destabilization of the tear film. Changes in cell membrane integrity can be measured clinically via measurements of lactate dehydrogenase enzyme release, fluorescein barrier permeability or other methods. Corneal epithelial cell membrane integrity is believed to be critical to maintain a tissue barrier function to prevent ocular infection.

Adverse changes in ocular tissues during contact lens wear also may arise due to exposure of ocular tissues to preservatives, disinfecting agents, cleaning agents and other components in the contact lens care solutions. This can occur through tissue contact with solutions which may directly contact ocular tissues during application or tissue contact with solutions which may adsorb or absorb to the contact lens during treatment of the contact lens by the solution, and subsequently desorb from the contact lens during wear into the eye.

Contact lens solutions have become complex formulations of multiple components which provide several functions. Attempts have been made to ameliorate the adverse effects of contact lenses and contact lens care solutions on ocular tissues, with mixed results. The best examples of success in changing contact lens care solutions to ameliorate their adverse effects on ocular tissues is represented by the creation of polymeric contact lens disinfecting agents, antimicrobial systems which do not bind to contact lens surfaces and the inclusion of water-soluble polymers and electrolytes such as potassium chloride, magnesium and calcium chloride into contact lens multi-purpose and rewetting solutions. However, despite these favorable changes in the compositions of contact lens care solutions, none provide perfect in-eye performance without some measure of adverse effect on ocular tissues. Some degree of compromise to the tear film, tissue or cellular membrane integrity, such as corneal epithelial cell membrane integrity, remains with all current contact lens care solutions. To date users have shown some preference for the polymeric quaternary ammonium systems, which combine three steps of cleaning, disinfecting and rinsing in one. However, such systems are usually weak in anti-fungal activities. Moreover, because of the positively charged nature of the quaternary ammonium, they tend to be heavily adsorbed or bound to the contact lens materials (which are usually negatively charged), causing eye irritation. Therefore, exists a need to improve contact lens care products to provide for simpler use with higher antimicrobial potency and less cornea irritation.

It is desirable to formulate a system having stronger antifungal properties than known systems, without increasing the adverse effects of contact lenses and contact lens care solutions on ocular tissues.

Unhoch et al., in U.S. Patent Application No. 2003/0189013 A1, entitled "Treatment of Circulating Water Systems," discloses a composition consisting of a mixture of polymeric biguanide and an alkylamine adjuvant for inhibiting the growth of or killing algae in a re-circulating system. The alkylamine has the following structure:

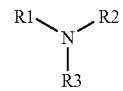

where R2 and R3 are each independent H or optionally substituted $C_{1-4}$ alkyl, and R1 is an optionally substituted $C_{8-12}$ or $C_{18-22}$ alkyl. Notably, Unhoch describes the alkylamine as an 'adjuvant' useful in re-circulating water systems, as opposed to an antimicrobial. Furthermore, an antimicrobial activity test against a five-microbial panel (as required by US FDA for contact lens disinfection) shows that dodecylamine (R1=$C_{12}$; R2, R3=H), having an antimicrobial activity far less than a more conventional cationically charged quaternary ammonium compound such as cetylpyridinium, is not qualified as a disinfectant for contact lens care.

A significant difference between contact lens care systems and re-circulating water system is that the former requires that a large amount of surfactant be present as a cleaning agent, while the latter is not compatible with surfactants due to foaming problems. Anionic surfactants and polymeric/non-polymeric quaternary ammonium form precipitate in aqueous solutions and, therefore, cannot be mixed. The presence of a non-ionic surfactant at a cleaning agent level usually would cause a significant, if not complete, loss of antimicrobial activity for non-polymeric quaternary ammonium or alkylamine. In fact, a non-ionic surfactant is commonly used in microbiology tests to stop quaternary ammonium/alkylamine activity during tests. Unhoch further teaches by implication that alkylamines with R1=$C_{13-17}$, which includes tetradecylamine, cannot be used in the polymeric biguanide/alkylamine mixture in a recirculating water system since they are insoluble in water. See, e.g. Experimental section and Table 4. Thus, the Unhoch reference does not teach or suggest that the claimed class of alkylamines would be useful in association with the cleaning of contact lenses.

In view of known limitations with contact lens care compositions, it would be advantageous to have contact lens care compositions, and methods of using the same, which are simpler to use, have higher antimicrobial potency, and show less corneal irritation.

DETAILED DESCRIPTION

New compositions for treating contact lenses have been discovered. The present compositions include, in an aqueous liquid medium, a non-ionic surfactant and an alkylamine having the following formula:

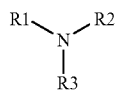

where R1 is a $C_{13-17}$ alkyl and R2 and R3 are each independently H or —$CH_3$. In an alternate embodiment of the present invention, R1 is a $C_{16-17}$ alkylamine, and R2 and R3 are each independently H or —$CH_3$. By way of example, when R1 is $C_{14}$, and R2 and R3 are H, the alkylamine is myristylamine, and when R1 is $C_{16}$, and R2 and R3 are H, the alkylamine is cetylamine.

Solutions according to the present invention may also include one or more of the following: additional antimicrobial components, preferably reduced in concentration from the concentration that is typically used with only one antimicrobial component; a buffer component in an amount effective to maintain the pH of the solution within a physiologically acceptable range; an effective amount of a viscosity inducing component; a surfactant in an amount effective to clean a contact lens contacted with the solution; and/or a tonicity component in an amount effective to provide the desired tonicity to the solution. The solutions may also include taurine. The benefits of including taurine are disclosed in U.S. patent application Ser. No. 10/328,641, to S. Huth, entitled "Contact Lens Care Compositions, Methods of Use, and Preparation which Protect Ocular Tissue," which is incorporated herein by reference. Such solutions provide the desired antimicrobial activity and performance effectiveness and, importantly, substantial, preferably enhanced, lens wearer/user comfort and acceptability benefits.

Specifically, it has been found that alkylamines having the following formula,

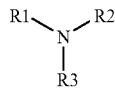

where R1 is a $C_{13-17}$ alkyl, and R2 and R3 are each independently H or —$CH_3$, has a high activity against fungi and certain bacteria. Such an application is hindered due to such alkylamines' lack of solubility in water. Based on the factors described below, the above-referenced alkylamine may be present in an amount in the range of about 0.1 ppm or about 0.3 ppm to about 7.5 ppm or about 10 ppm.

There are several obstacles which prevent the use of such antimicrobial agents in contact lens cleaning disinfecting application. First, contact lens cleaning and disinfecting solutions always contain significant amounts of surfactants in order to clean the contact lens surface which is contaminated mainly by tear protein and lipids. Of the three types of surfactants, nonionic surfactants are commonly used for contact lens cleaning. However, these are also commonly used to neutralize quaternary-based antimicrobial agents in microbiology test labs. Thus, the concentration must be carefully controlled.

Anionic surfactants such as soap are generally not compatible with quaternary amine based antimicrobials that are positively charged. In other words, it is common wisdom that the application of anionic surfactants would defy the microbial activity of non-polymeric based polyquaterniums. Electrostatic interaction between ion of the surfactant and cation of the quaternary ammonium would neutralize the net charge, eliminate the antimicrobial activity and form precipitate due to the loss of hydrophilicity by charge neutralization.

Cationic surfactants are compatible with alkyl amines, but they themselves are antimicrobial agents, and therefore cannot be added in sufficiently large amounts to dissolve the alkyl amine without irritating the eye. The inventors have unexpectedly discovered that alkylamines, especially those that are generally insoluble in water, are highly active in specific concentration ranges and can be used in contact lens disinfecting. That is, such alkylamines can be used for contact lens disinfection, provided that they are used with a certain type of surfactant which functions as a solubilizing agent, and the two are used according to a special mixing ratio. The inventors have further discovered that a certain type of non-ionic surfactants, used in a certain mixing ratio, can dissolve these water insoluble alkyl amines while maintaining anti-microbial effectiveness for disinfection. Furthermore, such contact lens disinfecting activity is significantly increased if polymeric quaternary amine such as Polyquaternium-1, poly [oxyethylene (dimethyliminio) ethylene-(dimethyliminio) ethylene dichloride], and a hexamethylene biguanide polymer are added.

The present compositions, which may be multi-purpose solutions, have a multitude of applications, for example, as disinfecting, cleaning, soaking, wetting, rewetting, rinsing, storing, in-the-eye cleaning, and conditioning compositions, for contact lens care, while providing substantial lens wearer/user comfort and acceptability. The present compositions also increase user compliance, that is promote regular and consistent contact lens care, and, ultimately, lead to or facilitate better ocular health. Any contact lenses, for example, conventional hard contact lenses, rigid gas permeable contact lenses and soft, hydrophilic or hydrogel, contact lenses, can be treated in accordance with the present invention.

Previously, it was believed that the afore-mentioned alkylamine was insoluble in aqueous solution, and hence undesirable for use in contact lens-care solutions. The inventors have unexpectedly discovered that the aforementioned alkylamines can be made soluble in aqueous solutions with non-ionic surfactants in an amount that will not neutralize the alkylamine antimicrobial activity. Preferred non-ionic surfactants include any non-ionic surfactants that contain an alkyl chain. Examples of some non-ionic surfactants for use in the present invention are disclosed in, for example, Kirk-Othmer, Encyclopedia of Chemical Technology, 3rd Edition, Vol. 22 (John Wiley E Sons, 1983), Sislet & Wood, Encyclopedia of Surface Active Agents (Chemical Publishing Co., Inc. 1964), McCutcheon's Emulsifiers & Detergents, North American and International Edition (McCutcheon Division, The MC Publishing Co., 1991), Ash, The Condensed Encyclopedia of Surfactants (Chemical Publishing Co., Inc., 1989), Ash, What Every Chemical Technologist Wants to Know About . . . Emulsifiers and Wetting Agents, Vol. 1 (Chemical Publishing Co., Inc., 1988), Tadros, Surfactants (Academic Press, 1984), Napper, Polymeric Stabilization of Colloidal Dispersion (Academic Press, 1983) and Rosen, Surfactants & Interfacial Phenomena, 2nd Edition (John Wiley & Sons, 1989), all of which are incorporated herein by reference. By way of example, but not of limitation, such surfactants include: Makon® 10 (Stepan Chemical Company, Chicago, Ill.), Lumulse® GR-40 (Lambent Technologies Inc., Norcross, Ga.), Lumulse® GRH-40 (Lambent Technologies Inc., Norcross, Ga.), Brij® 72 (Atlas Powder Company, Wilmington, Del.), Brij® 76 (Atlas Powder Company, Wilmington, Del.), Tween™ 80 (Uniquema (ICI Surfactants), Wilmington, Del.), Tween® 40, TPGS™ (Eastman Chemical Co., Kingsport, Tenn.), Cremophor® RH-40 (BASF Corporation, Mount Olive, N.J.), Tetronic®1304 (BASF Corporation, Mount Olive, N.J.), Tetronic® 1107 (BASF Corporation, Mount Olive, N.J.), Pluronic® F87 (BASF Corporation, Mount Olive, N.J.).

For example Myristylamine, an alkylamine of the class described above, ("MA") generally does not dissolve in water or in a basic solution. Furthermore, MA cannot be solubilized in surfactant micelles alone. MA is also insoluble in acid at ambient temperature, even with a solution pH below 2. However, if an acid and a surfactant which contains an alkyl chain coexist in a sufficient surfactant amount and the solution pH is below 6, MA may be dissolved in an aqueous solution. Once MA has been so dissolved, the solution pH may be increased, for example by adjusting the pH of the solution to neutral, without precipitating the MA.

The additional antimicrobial component may be any suitable, preferably ophthalmically acceptable, material effective to disinfect a contact lens contacted with the present solutions or alternatively adequately preserve a solution such as a contact lens rewetting solution. Preferably, the additional antimicrobial component is selected from biguanides, biguanides polymers, salts thereof and mixtures thereof, and is present in an amount in the range of about 0.1 ppm to about 3 ppm or less than 5 ppm (w/v). By way of example, and not of limitation, the additional antimicrobial component may be a monomeric quaternary ammonium or biguanide compound such as chlorhexidine digluconate, chlorhexidine diacetate, benzethonium chloride and myristamidopropyldimethylamine. The additional antimicrobial component may also be a polymeric quaternary ammonium compound such as Polyquad.® (polyquaternium-1) or poly [oxyethylene (dimethyliminio) ethylene-(dimethyliminio) ethylene dichloride] (sold under the trademark WSCP by Buckman Laboratories, Inc.). The preferred relatively reduced concentration of the additional antimicrobial component has been found to be very effective, in the present compositions, in disinfecting contact lenses contacted with the compositions, while at the same time promoting lens wearer/user comfort and acceptability.

Any suitable, preferably ophthalmically acceptable, surfactant component which is effective in cleaning contact lenses may be employed. The surfactant component preferably is non-ionic and, more preferably, is selected from poly (oxyethylene)-poly(oxypropylene) block copolymers and mixtures thereof.

Any suitable, preferably ophthalmically acceptable viscosity inducing or thickening agent may be included in the present compositions. The viscosity inducing component preferably is selected from cellulosic derivatives and mixtures thereof and is present in an amount in the range of about 0.05% or about 1.5% to about 3% or about 5.0% (w/v). Without wishing to limit the invention to any particular theory of operation, it is believed that the presence of a viscosity inducing component at least assists in providing the lens wearer/user comfort and acceptability benefits of the present invention, which promote regular and consistent contact lens care and ultimately lead to or facilitate better ocular health. The present combinations of components, for example, including such viscosity inducing components, are effective in providing the degree of lens wearer/user comfort and acceptability benefits described herein.

Although any suitable, necessarily ophthalmically acceptable, tonicity component may be employed, an extremely useful tonicity component is a combination of sodium chloride and potassium chloride.

The present compositions preferably include an effective amount of a chelating component. Any suitable, preferably ophthalmically acceptable, chelating component may be included in the present compositions, although ethylenediaminetetraacetic acid (EDTA), salts thereof and mixtures thereof are particularly effective. More preferably, the present compositions include chelating components in effective amounts less than about 0.05% (w/v) and still more preferably 0.02°s (w/v) or less. Such reduced amounts of chelating component in the present compositions remain effective in providing the desired chelating and/or sequestering functions while, at the same time, are better tolerated in the eye, thereby reducing the risk of user discomfort and/or ocular irritation.

Various combinations of two or more of the above noted components may be used in providing at least one of the benefits described herein. Therefore, each and every such combination is included within the scope of the present invention.

In one embodiment, the present compositions comprise: a liquid aqueous medium; an alkylamine having the following formula:

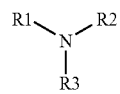

where R1 is a $C_{13-17}$ alkyl, and R2 and R3 are each independently H or —$CH_1$, in an amount effective to, in association with the remainder of the solution, disinfect a contact lens contacted with the composition; a surfactant, usually a non-ionic surfactant, component in an amount effective in cleaning a contact lens contacted with the composition; a boric buffer component in an amount effective in maintaining the pH of the composition within a physiologically acceptable range; an effective amount of a viscosity inducing component; and an effective amount of a tonicity component. The present compositions preferably include an effective amount of a chelating or sequestering component, more preferably in a range of less than 0.05% (w/v). Each of the components, in the concentration employed, included in the solutions and the formulated solutions of the present invention generally are ophthalmically acceptable. In addition, each of the components (in the case of the alkylamine, in combination with the anionic surfactant as described above), in the concentration employed included in the present solutions usually is soluble in the liquid aqueous medium. The solution may also optionally include an additional antimicrobial component in an amount effective to, in association with the remainder of the solution, disinfect a contact lens contacted with the composition.

A solution or component thereof is "ophthalmically acceptable" when it is compatible with ocular tissue, that is, it does not cause significant or undue detrimental effects when brought into contact with ocular tissue. Preferably, each component of the present compositions is also compatible with the other components of the present compositions. The present compositions are more preferably substantially ophthalmically optimized. An ophthalmically optimized composition is one which, within the constraints of component chemistry, minimizes ocular response, or conversely delivers ophthalmic benefit to the lens wearing eye.

The presently useful additional antimicrobial components include chemicals which derive their antimicrobial activity through a chemical or physiochemical interaction with microbes or microorganisms, such as those contaminating a contact lens. Suitable additional antimicrobial components are those generally employed in ophthalmic applications and include, but are not limited to, quaternary ammonium salts used in ophthalmic applications such as poly[dimethylimino-2-butene-1,4-diyl] chloride, alpha-[4-tris(2-hydroxyethyl)ammonium]-dichloride (chemical registry number 75345-27-6, available under, the trademark Polyquatemium 1® from Onyx Corporation), benzalkonium halides, and biguanides, such as salts of alexidine, alexidine-free base, salts of chlorhexidine, hexamethylene biguanides and their polymers, and salts thereof, antimicrobial polypeptides, chlorine dioxide precursors, and the like and mixtures thereof. Generally, the hexamethylene biguanide polymers (PHMB), also referred to as polyaminopropyl biguanide (PAPB), have molecular weights of up to about 100,000. Such compounds are known and are disclosed in Ogunbiyi et al, U.S. Pat. No. 4,759,595, the disclosure of which is hereby incorporated in its entirety by reference herein.

Generally, the antimicrobial component is present in the liquid aqueous medium at an ophthalmically acceptable or safe concentration such that the user can remove the disinfected lens from the liquid aqueous medium and thereafter directly place the lens in the eye for safe and comfortable wear. Alternatively, the antimicrobial component is present in the liquid aqueous medium at an ophthalmically acceptable or safe concentration and sufficient for maintaining preservative effectiveness. The antimicrobial components useful in the present invention preferably are present in the liquid aqueous medium in concentrations in the range of about 0.00001% to about 0.01% (w/v), and more preferably in concentrations in the range of about 0.00005% to about 0.001% (w/v) and most preferably in concentrations in the range of about 0.00005% to about 0.0005% (w/v).

The additional antimicrobial components suitable for inclusion in the present invention include chlorine dioxide precursors. Specific examples of chlorine dioxide precursors include stabilized chlorine dioxide (SCD), metal chlorites, such as alkali metal and alkaline earth metal chlorites, and the like and mixtures thereof. Technical grade sodium chlorite is a very useful chlorine dioxide precursor. Chlorine dioxide containing complexes such as complexes of chlorine dioxide with carbonate, chlorine dioxide with bicarbonate and mixtures thereof are also included as chlorine dioxide precursors. The exact chemical composition of many chlorine dioxide precursors, for example, SCD and the chlorine dioxide complexes, is not completely understood. The manufacture or production of certain chlorine dioxide precursors is described in McNicholas, U.S. Pat. No. 3,278,447, which is incorporated in its entirety herein by reference. Specific examples of useful SCD products include that sold under the trademark Dura Klor® by Rio Linda Chemical Company, Inc., and that sold under the trademark Anthium Dioxide® by International Dioxide, Inc.

If a chlorine dioxide precursor in included in the present compositions, it generally is present in an effective preservative or contact lens disinfecting amount. Such effective preservative or disinfecting concentrations usually are in the range of about 0.002 to about 0.06% (w/v) of the present compositions. The chlorine dioxide precursors may be used in combination with other antimicrobial components, such as biguanides, biguanide polymers, salts thereof and mixtures thereof.

In the event that chlorine dioxide precursors are employed as antimicrobial components, the compositions usually have an osmolality of at least about 200 mOsmol/kg and are buffered to maintain the pH within an acceptable physiological range, for example, a range of about 6 to about 10.

In one embodiment, the additional antimicrobial component is non-oxidative. It has been found that reduced amounts of non-oxidative antimicrobial components, for example, in a range of about 0.1 ppm to about 3 ppm or less than 5 ppm (w/v), in the present compositions are effective in disinfecting contact lenses and reduce the risk of such antimicrobial components causing ocular discomfort and/or irritation. Such reduced concentration of antimicrobial component is very useful when the antimicrobial component employed is selected from biguanides, biguanide polymers, salts thereof and mixtures thereof.

When a contact lens is desired to be disinfected by the present compositions, a total amount of antimicrobial component(s) effective to disinfect the lens is used. Generally, such an effective amount of the antimicrobial component reduces the microbial burden or load on the contact lens by one log order in three hours. More preferably, an effective amount of the disinfectant reduces the microbial load by one log order in one hour.

The buffer component is present in an amount effective to maintain the pH of the composition or solution in the desired range, for example, in a physiologically acceptable range of about 6 to about 7.5 or about 8.5. In particular, the solution has a pH in the range of about 7 to about 8. The buffer component preferably includes one or more phosphate or tromethamine (TRIS, 2-amino-2-hydroxymethyl-1,3-propanediol) or boric or boric/sodium borate buffers, for example, combinations of monobasic phosphates, dibasic phosphates and the like, or tromethamine and tromethamine hydrochloride. Particularly useful phosphate buffers are those selected from phosphate salts of alkali and/or alkaline earth metals. Examples of suitable phosphate buffers include one or more of sodium phosphate dibasic ($Na_2HPO_4$) sodium phosphate monobasic ($NaH_2PO_4$) and potassium phosphate monobasic ($KH_2PO_4$). The buffer component may also include an amino acid such as taurine. The present buffer components frequently are used in amounts in a range of about 0.01% or about 0.02% to about 0.5% or about 1% (w/v), calculated as phosphate ion.

The present compositions usually further comprise effective amounts of one or more additional components, such as a detergent or surfactant component; a viscosity inducing or thickening component; a chelating or sequestering component; a tonicity component; and the like and mixtures thereof. The additional component or components may be selected from materials which are known to be useful in contact lens care compositions and are included in amounts effective to provide the desired effect or benefit. When an additional component is included, it is generally compatible under typical use and storage conditions with the other components of the composition. For instance, the aforesaid additional component or components are substantially stable in the presence of the antimicrobial and buffer components described herein.

A surfactant component generally is present in an amount effective in cleaning, that is to at least facilitate removing, and preferably effective to remove, debris or deposit material from, a contact lens contacted with the surfactant containing solution. Exemplary surfactant components include, but are not limited to, non-ionic surfactants, for example, polysorbates (such as polysorbate 20-Trademark Tween 20), 4-(1,1,3,3-tetramethylbutyl)phenol/poly(oxyethylene) polymers (such as the polymer sold under the trademark Tyloxapol), poly(oxyethylene)-poly(oxypropylene) block copolymers, glycolic esters of fatty acids and the like, and mixtures thereof.

The surfactant component is generally non-ionic, and usually is selected from poly(oxyethylene)-poly(oxypxopylene) block copolymers and mixtures thereof. Such surfactant components can be obtained commercially from the BASF Corporation under the trademarks Pluronic® and Tetronic®.

Such block copolymers can be generally described as polyoxyethylene/polyoxypropylene condensation polymers terminated in primary hydroxyl groups. They may be synthesized by first creating a hydrophobe of desired molecular weight by the controlled addition of propylene oxide to the two hydroxyl groups of propylene glycol or glycerin. In the second step of the synthesis, ethylene oxide is added to sandwich this hydrophobe between hydrophile groups.

In accordance with a more preferred embodiment of the invention, such block copolymers having molecular weights in the range of about 2500 to 30,000 daltons are suitable, with a molecular weight range of about 6000 to about 15,000 daltons being still more preferred. Specific examples of surfactants which are satisfactory include: poloxamer 108 (BASF Corporation, Mount Olive, N.J.), poloxamer 188, poloxamer 237, poloxamer 238, poloxamer 288, poloxamer 407, Tetronic 1107, Tetronic 1304, Tetronic 1307. Particularly good results are obtained poloxamer 237.

The amount of surfactant component, if any, present varies over a wide range depending on a number of factors, for example, the concentration of the alkyl amine being used, the specific surfactant or surfactants being used, the other components in the composition and the like. Often the amount of surfactant is in the range of about 0.005% or about 0.01% to about 0.1% or about 0.5% or about 1.0% (w/v).

The viscosity inducing components employed in the present solutions preferably are effective at low or reduced concentrations, compatible with the other components of the present solutions, and anionic. Such viscosity inducing components are effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the treated contact lens. The viscosity inducing component may also act to cushion the impact on the eye surface during insertion and serves also to alleviate eye irritation.

Suitable viscosity inducing components include, but are not limited to, water soluble natural gums, cellulose-derived polymers and the like. Useful natural gums include guar gum, gum tragacanth and the like. Useful cellulose-derived viscosity inducing components include cellulose-derived polymers, such as hydroxypropyl cellulose, hydroxypropylmethyl cellulose, carboxymethyl cellulose, methyl cellulose, hydroxyethyl cellulose and the like. More preferably, the viscosity inducing agent is selected from cellulose derivatives (polymers) and mixtures thereof. A very useful viscosity inducing component is hydroxypropylmethyl cellulose (HPMC).

The viscosity inducing component is used in an amount effective to increase the viscosity of the solution, preferably to a viscosity in the range of about 1.5 to about 30, or even as high as about 750, cps at 25° C., preferably as determined by USP test method No. 911 (USP 23, 1995). To achieve this range of viscosity increase, an amount of viscosity inducing component of about 0.01% to about 5% (w/v) preferably is employed, with amounts of about 0.05% to about 0.5% being more preferred.

A chelating or sequestering component preferably is included in an amount effective to enhance the effectiveness of the antimicrobial component and/or to complex with metal ions to provide more effective cleaning of the contact lens.

A wide range of organic acids, amines or compounds which include an acid group and an amine function are capable of acing as chelating components in the present compositions. For example, nitrilotriacetic acid, diethylenetriaminepentacetic acid, hydroxyethylethylene-diaminetriacetic acid, 1,2-diaminocyclohexane tetraacetic acid, hydroxyethylaminodiacetic acid, ethylenediamine-tetraacetic acid and its salts, polyphosphates, citric acid and its salts, tartaric acid and its salts, and the like and mixtures thereof, are useful as chelating components. Ethylenediaminetetraacetic acid (EDTA) and its alkali metal salts, are preferred, with disodium salt of EDTA, also known as disodium edetate, being particularly preferred.

The chelating component preferably is present in an effective amount, for example, in a range of about 0.01% and about 1% (w/v) of the solution.

In a very useful embodiment, particularly when the chelating component is EDTA, salts thereof and mixtures thereof, a reduced amount is employed, for example, in the range of less than about 0.05% (w/v) or even about 0.02% (w/v) or less. Such reduced amounts of chelating component have been found to be effective in the present compositions while, at the same time, providing for reduced discomfort and/or ocular irritation.

The liquid aqueous medium used is selected to have no substantial deleterious effect on the lens being treated, or on the wearer of the treated lens. The liquid medium is constituted to permit, and even facilitate, the lens treatment or treatments by the present compositions. The liquid aqueous medium advantageously has an osmolality in the range of at least about 200-mOsmol/kg to about 300 or about 350 mOsmol/kg. The liquid aqueous medium more preferably is substantially isotonic or hypotonic (for example, slightly hypotonic) and/or is ophthalmically acceptable.

The liquid aqueous medium preferably includes an effective amount of a tonicity component to provide the liquid medium with the desired tonicity. Such tonicity components may be present in the liquid aqueous medium and/or may be introduced into the liquid aqueous medium. Among the suitable tonicity adjusting components that may be employed are those conventionally used in contact lens care products, such as various inorganic salts. Sodium chloride and/or potassium chloride and the like are very useful tonicity components. The amount of tonicity component included is effective to provide the desired degree of tonicity to the solution. Such amount may, for example, be in the range of about 0.1% to about 1.5% (w/v). If a combination of sodium chloride and potassium chloride is employed, it is preferred that the weight ratio of sodium chloride to potassium chloride be in the range of about 2.5 to about 6 or about 8.

The amount of taurine useful in the present invention may be determined by objective clinical measures such as tear LDH release from corneal epithelial cells or fluorescein barrier permeability measurements or another means to evaluate ocular cell membrane integrity such as fluorescein or rose bengal staining. Yet another means to evaluate ocular cell membrane integrity is the use of confocal microscopy to measure epithelial cell area. In lieu of using tear LDH as a response factor, another inflammatory mediator may be measured in tears to indicate a beneficial effect from taurine. Useful amounts of taurine can also be determined by subjective clinical measures such as itching, lacrimation (tearing) and comfort. The amount of taurine useful in the present invention is generally from about 0.01 to about 2.0 w/v %. The preferred amount is 0.05 to 1.00 w/v %.

Methods for treating a contact lens using the herein described compositions are included within the scope of the invention. Such methods comprise contacting a contact lens with such a composition at conditions effective to provide the desired treatment to the contact lens.

The contacting temperature is preferred to be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time in the range of about 5 minutes or about 1 hour to about 12 hours or more.

The contact lens can be contacted with the liquid aqueous medium by immersing the lens in the medium. During at least a portion of the contacting, the liquid medium containing the contact lens optionally may be agitated, for example, by shaking the container containing the liquid aqueous medium and contact lens, to at least facilitate removal of deposit material from the lens. After such contacting step, the contact lens optionally may be manually rubbed to remove further deposit material from the lens. The cleaning method optionally may also include rinsing the lens substantially free of the liquid aqueous medium prior to returning the lens to a wearer's eye.

The following examples, while not limiting, are illustrative of the invention.

The following is the procedure by which various antimicrobial agents and solutions are tested for their ability to reduce microbial loads over short periods of time, typically 24 hours and less. The procedure is a basic microbiology challenge test, which involves the inoculation of test product aliquots with a known number of viable cells of several test organisms, and assay for the survivors at various time intervals. The results are used to calculate log drops at soak times and construct kill-curves (graphs of survivors versus time) if desired.

*Candida albicans*, ATCC 10231, is one of five organisms specified per FDA and ISO/CLI tests for the testing of contact lens disinfectants (FDA Premarket Notification (510 k) Guidance Document for Contact Lens Care Products, Appendix B1, Apr. 1, 1997 and ISO/FDIS 14729: Ophthalmic optics—Contact lens care products—Microbiological requirements and test methods for products and regimens for hygienic management of contact lenses, January 2001). Contact lens disinfectants are also known as contact lens multi-purpose solutions when they are used for rinsing, cleaning, disinfection, storage and rewetting contact lenses. The five FDA/ISO specified test organisms are listed below:

*Serratia marcesans*, ATCC 13880
*Staphylococcus aureus*, ATCC 6538
*Pseudomonas aeruginosa*, ATCC 9027
*Candida albicans*, ATCC 10231
*Fusarium solani*, ATCC 36031

*Candida albicans* is often the most resistant of the five organisms to commonly used cationic antimicrobial agents in contact lens multi-purpose solutions. Thus, achievement of adequate antimicrobial activity against *Candida* is often the most difficult task to pass a particular disinfection efficacy standard. FDA and ISO guidelines specify two disinfection efficacy standards, indicated in the table below:

| Organism | Average log reduction at labeled soak time |
|---|---|
| Stand Alone Disinfectant (Primary) Criteria: | |
| S. marcescens | 3.0 logs |
| S. aureus | 3.0 logs |
| P. aeruginosa | 3.0 logs |
| C. albicans | 1.0 log |
| F. solani | 1.0 log |

| Organism | Average log reduction at labeled soak time |
|---|---|
| Regimen-Dependent Disinfectant (Secondary) Criteria: | |
| S. marcescens | Minimum of 1.0 log per bacterium, |
| S. aureus | sum of all three bacteria log-drops |
| P. aeruginosa | must be greater than or equal to 5.0 log |
| C. albicans | Stasis |
| F. solani | Stasis |

The specific test procedure for testing antimicrobial activity against the five FDA/ISO specified test organisms is as follows (*C. albicans* is provided as a specific example): Test samples are sterile-filtered through a 0.22 micron sterile filter into sterile plastic high density polyethylene bottles or plastic flasks. A 10-mL aliquot of test sample is aseptically transferred into a sterile polystyrene plastic test tube. Sterile saline (0.90 w/v % NaCl) with 0.05 w/v % Polysorbate 80 (SS+TWEEN) is transferred into a separate control tube. All samples and control are stored at 20-25° C. throughout the duration of the test.

Test cultures of *Candida albicans*, ATCC 10231 are prepared in the conventional manner. *Candida albicans* cultures are grown on agar slants from primary frozen, lyophilized or "Culti-loop®" cultures. Three mL of sterile 0.9% saline is used to gently dislodge culture growth from the agar surface. The resulting harvest is transferred to an appropriate screw cap test tube containing glass beads and vortexed for approximately one minute. The vortexed harvest is diluted as needed with sterile 0.9% saline to prepare the culture inoculum with a concentration of $1\times10e8$ CFU/mL. Fifty microliters of culture inoculum is added to 10.0 mL of each test sample and control, so that the final inoculum level is in the range of $1\times10e5$ to $1\times10e6$ CFU (colony forming units) per mL of *Candida albicans*, ATCC 10231. Each sample and control tube is vortexed briefly to disperse the inoculum. Contact time intervals for testing activity against *Candida* are typically 4 or 6 hours, to conform to the intended product label instructions for contact lens soak time.

Aerobic Plate Count Methods are performed in order to quantitate test samples for their levels of survivors. At appropriate assay times, 0.5 mL well-vortexed aliquots are removed from sample tubes and added to glass test tubes containing 4.5 mL Letheen Neutralizing Broth media (Berton, Dickinson and Company, Sparks, Md.). After a previously determined, validated neutralizing time period, these samples are diluted 10-fold through serial dilutions using glass test tubes containing 4.5 mL Letheen Neutralizing Broth media. Aliquots of 0.1 mL are removed from each dilution tube and spread-plate applied to agar plates containing Sabouraud Dextrose Agar (SAB) (Berton, Dickinson and Company, Sparks, Md.). $10^1$ to $10^4$ CFU/mL survivor levels are quantitated. The SS+TWEEN control samples are quantitated only at time=0 using 3 serial 10-fold dilutions, in order to determine the actual levels of challenge organisms initially present per mL of sample (initial inoculum). Recovery agar plates are incubated at 20-25° C. for 3-5 days.

Numbers of colony-forming-units (CFU) are counted for each countable agar plate (generally between 8-80 colonies per plate for *Candida* plates). Log-drops in CFU/mL are determined for each sample at each time interval by converting the total number of survivors at each time interval to a base-10 logarithm and subtracting this from the base-10 logarithm equivalent of the initial inoculum of the SS+TWEEN control. Log reduction values can be plotted against contact time (the particular test time interval) or evaluated as is.

EXAMPLE 1

As noted above in the Background of the Invention section, non-ionic surfactants are commonly used in microbiology tests to stop a quaternary ammonium/alkylamine activity. One of the significant differences between contact lens care system and re-circulating water systems is that the former requires the presence of a large amount of a surfactant as a cleaning agent while the latter is not compatible with surfactants due to foaming problems. Anionic surfactant and polymeric/non-polymeric quaternary ammoniums form ion-pair or precipitate in an aqueous solution and therefore, cannot be mixed together. The presence of non-ionic surfactant at a cleaning agent level usually would cause a significant, if not complete, loss of antimicrobial activity for non-polymeric quaternary ammonium or alkylamine. As shown in Table 1, the addition of the non-ionic surfactant tocopherol polyethylene glycol succinate ("TPGS") halts the ammonium/alkylamine activity.

TABLE 1

| Formulation | w/v % | w/v % |
|---|---|---|
| Cetylpyridinium Chloride | 0.001 | 0.001 |
| TPGS | 0 | 0.025 |
| Taurine | 0.05 | 0.05 |
| Propylene Glycol | 0.50 | 0.50 |
| Tetronic ® 1307 | 0.05 | 0.05 |
| NaEDTA | 0.01 | 0.01 |
| HPMC | 0.15 | 0.15 |
| Tris | 0.021 | 0.021 |
| Tris.HCl | 0.055 | 0.055 |
| NaCl | 0.65 | 0.65 |
| KCl | 0.14 | 0.14 |
| | Log Drop | Log Drop |
| C. albicans | 4.41 | 0.12 |
| F. solani | >4.08 | 1.06 |

EXAMPLE 2

The formulations shown in Table 2A were evaluated for their antimicrobial activity for contact lens disinfecting. As may be seen, this formulation exhibited a very high antimicrobial activity.

TABLE 2A

| Ingredient | % w/w | % w/w |
|---|---|---|
| Myristylamine | 0.0003 | 0.0005 |
| Tetronic ® 1307 | 0.05 | 0.05 |
| HPMC | 0.15 | 0.15 |
| Propylene Glycol | 0.5 | 0.5 |
| Tris | 0.021 | 0.021 |
| Tris.HCl | 0.055 | 0.055 |
| NaCl | 0.65 | 0.65 |
| KCl | 0.14 | 0.14 |
| pH 7.8 | | |
| | Log Drop | Log Drop |
| S. marcescens | 1.18 | 2.6 |
| S. aureus | 2.87 | 4.8 |
| P. aeruginosa | >4.63 | >4.63 |

TABLE 2A-continued

| C. albicans | 3.67 | 4.41 |
|---|---|---|
| F. solani | >4.34 | >4.34 |

It is easily seen from the data in Table 2 that the myristylamine has strong antimicrobial activity against *C. albicans*, as well as other organisms.

In contrast as shown in Table 2B, Dodecylamine, a C12 primary amine which is water soluble, has very weak antimicrobial activity and, therefore, not suitable as a disinfectant for contact lens cleaning and disinfecting.

TABLE 2B

| Ingredient | % w/w | % w/w |
|---|---|---|
| Dodecylamine | 0.0005 | 0.0003 |
| Taurine | 0.05 | 0.05 |
| Propylene Glycol | 0.50 | 0.50 |
| Tetronic 1307 | 0.05 | 0.05 |
| NaEDTA | 0.01 | 0.01 |
| HPMC | 0.15 | 0.15 |
| Tris | 0.021 | 0.021 |
| Tris.HCl | 0.055 | 0.055 |
| NaCl | 0.65 | 0.65 |
| KCl | 0.14 | 0.14 |
| pH 7.8 | | |
| | Log drop | Log drop |
| S. marcesens | 0.46 | 0.46 |
| S. aureus | 0.12 | 0.34 |
| P. aeruginosa | 1.36 | 1.4 |
| C. albicans | 1.77 | 0.91 |
| F. solani | 0.16 | 0.09 |

EXAMPLE 3

As shown by the formulations and resulting log reductions shown in Table 3, the antimicrobial activity of an alkylamine having the following formula:

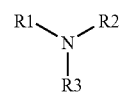

where R1 is a $C_{13-17}$ alkyl and R2 and R3 are each independently H or —$CH_3$, may be further enhanced if one or more other types of antimicrobial agents are added.

TABLE 3

| Formulation | w/v % | w/v % |
|---|---|---|
| Myristylamine | 0.0005 | 0.0005 |
| WSCP | 0.001 | 0.0 |
| NaClO$_2$ | 0.01 | 0.0 |
| NaCitrate | 0.4 | 0.0 |
| Taurine | 0.05 | 0.05 |
| Propylene Glycol | 0.50 | 0.50 |
| T1307 | 0.05 | 0.05 |
| HPMC | 0.15 | 0.15 |
| Tris | 0.021 | 0.021 |
| Tris.HCl | 0.055 | 0.055 |

TABLE 3-continued

| | | |
|---|---|---|
| NaCl | 0.65 | 0.65 |
| KCl | 0.14 | 0.14 |
| | Log Drop | Log Drop |
| S. marcescens | 3.1 | 1.68 |
| S. aureus | 3.74 | 2.93 |
| P. aeruginosa | >4.63 | >4.63 |
| C. albicans | 2.95 | 3.29 |
| F. solani | >4.34 | >4.34 |

These results are collaborated by the formulation and resulting log reductions shown in Table 4, and by the formulations and resulting log reductions shown in Table 5.

TABLE 4

| Formulation | w/v % | w/v % |
|---|---|---|
| Myristylamine | 0.0003 | 0.0003 |
| PHMB | 0 | 0.00003 |
| Taurine | 0.05 | 0.05 |
| Propylene Glycol | 0.50 | 0.50 |
| Tetronic 1107 | 0.05 | 0.05 |
| HPMC | 0.15 | 0.15 |
| Tris | 0.021 | 0.021 |
| Tris.HCl | 0.055 | 0.055 |
| NaCl | 0.65 | 0.65 |
| KCl | 0.14 | 0.14 |
| pH 7.8 | | |
| | Log Drop | Log Drop |
| S. marcescens | 1.18 | 3.46 |
| S. aureus | 2.87 | 4.21 |
| P. aeruginosa | >4.63 | >4.63 |
| C. albicans | 3.67 | 3.31 |
| F. solani | >4.34 | >4.34 |

TABLE 5

| Formulation | w/v % |
|---|---|
| Myristylamine | 0.0005 |
| Polyquaternium-1 | 0.001 |
| NaCitrate | 0.6 |
| Taurine | 0.05 |
| Propylene Glycol | 0.50 |
| Tetronic ® 1304 | 0.05 |
| HPMC | 0.15 |
| Tris | 0.021 |
| Tris.HCl | 0.055 |
| NaCl | 0.65 |
| KCl | 0.14 |
| pH 7.8 | |
| | Log Drop |
| S. marcescens | 3.64 |
| S. aureus | 4.69 |
| P. aeruginosa | >4.63 |
| C. albicans | 4.52 |
| F. solani | >4.34 |

EXAMPLE 4

As discussed in greater detail above, the inventors have discovered that a certain type of non-ionic surfactants (certain mixing ratios) can dissolve these water insoluble alkylamines while maintaining anti-microbial effectiveness for disinfection. Specifically, water insoluble alkylamines having the following formula,

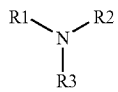

where R1 is a $C_{13-17}$ alkyl and R2 and R3 are each independently H or —$CH_3$, may be dissolved in aqueous solution without neutralization of the antimicrobial activity by the surfactant. The maximum surfactant:antimicrobial ratio above which the antimicrobial activities will be significantly neutralized varies depending on the hydrophobicity/hydropholicity of the surfactant and the amount of the antimicrobial. For an ordinary surfactant with at least one alkyl chain, such as Tween 80 and TPGS, this maximum surfactant:antimicrobial ratio is about 7-20 when the alkylamine concentration is not more than 10 ppm. One of ordinary skill in the art can determine the maximum surfactant alkylamine ratio for other surfactant systems based on the disclosure contained herein.

Table 6 shows that the 10 ppm MA solutions fail to meet the stand-alone criteria when the Tween 80:MA ratio is at 7.4. For TPGS, the maximum surfactant:MA ratio is about 20 (see Table 8). However, with the addition of a second antimicrobial, Polyquatemium-1, the solution can still be a stand-alone disinfectant product.

TABLE 6

| Formulation | % w/w | % w/w |
|---|---|---|
| Tween 80 | 0.0074 | 0.0074 |
| Myristylamine | 0.001 | 0.001 |
| Polyquaternium-1 | 0 | 0.000075 |
| Taurine | 0.05 | 0.05 |
| Propylene Glycol | 0.5 | 0.5 |
| Tetronic ® 1307 | 0.05 | 0.05 |
| $Na_2EDTA$ | 0.01 | 0.01 |
| HPMC | 0.15 | 0.15 |
| $Na_2HPO_4 \cdot 7H2O$ | 0.12 | 0.12 |
| $NaH_2PO_4 \cdot H2O$ | 0.01 | 0.01 |
| NaCl | 0.55 | 0.55 |
| KCl | 0.14 | 0.14 |
| pH 7.3 | | |
| | Log drop at 6 hour | |
| S. marcescens 36031 | 1.19 | 3.12 |
| S. aureurs 6538 | 1.04 | 3.21 |
| P. aeruginosa 9027 | >4.58 | >4.58 |
| C. albicans 10231 | >4.67 | >4.67 |
| F. solani 36031 | 3.73 | 3.12 |

However, when the surfactant and alkylamine are present in a ratio of 20, anti-fungal activity is not so reduced. Solution #5 shown in Table 7 (compared with solution #6 that only differs in the TPGS content) contains surfactant and alkylamine in a ratio of (TPGS:MA) of 20. As shown in Table 7, when the surfactant:alkylamine ratio is 20, anti-fungal activity (Ca and Fs) remains.

TABLE 7

| Formulation | #5 w/v % | #6 w/v % |
|---|---|---|
| Myristylamine | 5 ppm | 5 ppm |
| TPGS | 0.01 | 0 |
| Taurine | 0.05 | 0.05 |
| Propylene Glycol | 0.50 | 0.50 |
| Tetronic ® 1307 | 0.05 | 0.05 |
| NaEDTA | 0.01 | 0.01 |
| HPMC | 0.15 | 0.15 |

TABLE 7-continued

| | | |
|---|---|---|
| Tris | 0.021 | 0.021 |
| Tris.HCl | 0.055 | 0.055 |
| NaCl | 0.65 | 0.65 |
| KCl | 0.14 | 0.14 |
| pH 7.8 | | |

| | Log Drop | Log Drop |
|---|---|---|
| S. marcesens | 0.99 | 2.6 |
| S. aureus | 2.57 | 4.8 |
| P. aeruginosa | 4.86 | 4.86 |
| C. albicans | 4.41 | 4.41 |
| F. solani | 2.5 | 3.43 |

Furthermore, as shown in Table 8A, the anti-fungal activity (Ca and Fs) was still seen at the TPGS:MA ratio of up to 60. However, the anti-bacteria activity lost considerably at the TPGS:MA ratio of 40. Thus, one of ordinary skill in the art may carefully tailor the solution to the desired antimicrobial activity. Such tailoring may be achieved, for example, by controlling the alkylamine content or by adding additional antimicrobials into solution.

TABLE 8A

| Formulation | #3 % w/w | #2 % w/w | #4 % w/w |
|---|---|---|---|
| Myristylamine | 0.001 | 0.001 | 0.001 |
| TPGS | 0.06 | 0.04 | 0.02 |
| Taurine | 0.05 | 0.05 | 0.05 |
| Propylene Glycol | 0.50 | 0.50 | 0.50 |
| Tetronic ® 1307 | 0.05 | 0.05 | 0.05 |
| NaEDTA | 0.01 | 0.01 | 0.01 |
| HPMC | 0.15 | 0.15 | 0.15 |
| Tris | 0.021 | 0.021 | 0.021 |
| Tris.HCl | 0.055 | 0.055 | 0.055 |
| NaCl | 0.65 | 0.65 | 0.65 |
| KCl | 0.14 | 0.14 | 0.14 |
| pH 7.8 | | | |

| | Log Drop | Log Drop | Log Drop |
|---|---|---|---|
| S. marcesens | 0.46 | 0.67 | 2.2 |
| S. aureus | 0.22 | 1.31 | 4.5 |
| P. aeruginosa | 2.32 | 3.72 | 4.26 |
| C. albicans | 3.72 | 4.41 | 4.41 |
| F. solani | 2.76 | 2.52 | 3.73 |

As shown in Table 8B, the surfactant:antimicrobial ratio can be more than 500 when surfactant is a Tetronic® or Pluronic®. Such ratio may be explained, perhaps, by the fact that neither of these surfactants contain an alkyl chain.

TABLE 8B

| | % w/w | % w/w | % w/w | % w/w |
|---|---|---|---|---|
| Cetylamine | 0.0001 | 0.0001 | 0.000125 | 0.0003 |
| PHMB | 0.00 | 0.00002 | 0.00 | 0.00 |
| Boric acid | 0.6 | 0.6 | 0.6 | 0.6 |
| NaCl | 0.59 | 0.59 | 0.59 | 0.59 |
| HPMC | 0.15 | 0.15 | 0.15 | 0.15 |
| Edetate Disodium | 0.01 | 0.01 | 0.01 | 0.01 |
| Taurine | 0.05 | 0.05 | 0.05 | 0.05 |
| NaCl | 0.59 | 0.59 | 0.59 | 0.59 |
| KCl | 0.14 | 0.14 | 0.14 | 0.14 |
| Pluronic ® F87 | 0.05 | 0.05 | 0.05 | 0.05 |
| PEG 400 | 0.2 | 0.2 | 0.2 | 0.2 |
| NaOH adjust pH to 7.7 | | | | |

| | Log Drop | Log Drop | Log Drop | Log Drop |
|---|---|---|---|---|

TABLE 8B-continued

| | | | | |
|---|---|---|---|---|
| S. marcescens 13880 | 2.35 | 4.18 | 3.76 | 3.61 |
| S. aureus 6538 | 4.18 | 4.81 | 4.81 | 4.79 |
| P. aeruginosa 9027 | 4.49 | 4.43 | 3.95 | 4.49 |
| C. albicans 10231 | 2.89 | 1.51 | 1.97 | 2.89 |
| F. solani 36031 | 1.3 | 1.14 | 2.76 | 1.48 |

EXAMPLE 5

Another benefit of the present invention that has been discovered by the inventors is that alkylamines having the following formula:

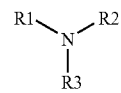

where R1 is a $C_{13-17}$ alkyl, and R2 and R3 are each independently H or —$CH_3$, have a significantly lower contact tens uptake than other types of quaternary ammonium or tertiary amines. As a result, eye irritation can be significantly reduced.

The results in Table 9A show the remaining quaternary ammonium and tertiary amine content left in solution after a 15 ml-solution-2 lenses closed system has been shaken for 6 days at room temperature. The "Without Lens" column shows the remaining quaternary ammonium and tertiary amine content left in solution after the identical 15 ml-system (minus the lenses) was shaken under identical conditions. The control which was run for this experiment, which includes the remaining ingredients in the solutions referenced in Table 9A are listed in Table 9B. As one of ordinary skill in the art would realize, the less quaternary ammonium or tertiary amine content remaining in solution after the shaking period, the higher the absorption by the lenses.

TABLE 9A

| | Without Lens | Acuvue | Purevision |
|---|---|---|---|
| Armeen 12D (Dodecylamine) | 44.4 ppm | 35.0 ppm | 14.1 ppm |
| Myristylamine, (TPGS 20 fold) | 37.9 ppm | 34.1 ppm | 13.0 ppm |
| Myristylamidopropyldimethylamine | 43.5 ppm | 18.2 ppm | 4.7 ppm |
| Cetylpyridium chloride | 42.7 ppm | 3.3 ppm | 1.3 ppm |

TABLE 9B

| Placebo for the solutions in Table 9a | % w/w |
|---|---|
| Taurine | 0.05 |
| Propylene Glycol | 0.50 |
| T1307 | 0.05 |
| HPMC | 0.15 |
| Tris | 0.021 |
| Tris.HCl | 0.055 |
| NaCl | 0.65 |
| KCl | 0.14 |
| D.I water | 98.38 |
| pH 7.8 | |

The solutions according to the above examples may be used, for example, to clean contact lenses. In this embodiment of the invention, approximately three (3) ml of this solution is introduced into a lens vial containing a lipid, oily deposit laden, hydrophilic or soft contact lens. The contact lens is maintained in this solution at room temperature for at least about four (4) hours. This treatment is effective to disinfect the contact lens. In addition, it is found that a substantial portion of the deposits previously present on the lens has been removed. This demonstrates that this solution has substantial passive contact lens cleaning ability. Passive cleaning refers to the cleaning which occurs during soaking of a contact lens, without mechanical or enzymatic enhancement.

After this time, the lens is removed from the solution and is placed in the lens wearer's eye for safe and comfortable wear. Alternately, after the lens is removed from the solution, it is rinsed with another quantity of this solution and the rinsed lens is then placed in the lens wearer's eye for safe and comfortable wear.

Alternatively, the solutions provided in the above-referenced examples may be used, for example, to wet or rewet contact lenses. A hydrophilic contact lens is ready for wear. In order to facilitate such wearing, one or two drops of one of the above solutions is placed on the lens immediately prior to placing the lens in the lens wearer's eye. The wearing of this lens is comfortable and safe.

Alternatively, a lens wearer wearing a contact lens may apply one or two drops of one of the above solutions in the eye wearing the lens. This effects a re-wetting of the lens and provides for comfortable and safe lens wear.

While this invention has been described with respect to various specific examples and embodiments, it is to be understood that the invention is not limited thereto and that it can be variously practiced within the scope of the following claims.

What is claimed is:

1. A method for maintaining ocular tissue cell membrane integrity during contact lens wear comprising:
   contacting the lens with an aqueous solution comprising from about 0.1 to about 10 ppm of a primary, secondary, or tertiary alkylamine having the following formula

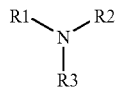

where R1 is a $C_{13-17}$ alkyl, and R2 and R3 are each independently H or —$CH_3$; and
   a non-ionic surfactant in an amount effective to render the alkylamine soluble in the aqueous solution.

2. The method for disinfecting of claim 1, wherein the alkylamine is selected from the group consisting of myristylamine and cetylamine.

3. The method for disinfecting claim 1, wherein the non-ionic surfactant is a polyoxypropylene-polyoxyethylene co-block polymer.

4. The method for disinfecting of claim 1, where in the aqueous solution further comprises a component selected from the group consisting of a second antimicrobial agent, a viscosity inducing agent, a chelating agent, a buffer, taurine and a tonicity component.

5. A method for maintaining ocular tissue cell membrane integrity during contact lens wear comprising contacting a lens positioned in a user's eye with an isotonic aqueous solution comprising:
   an aqueous liquid medium;
   a first antimicrobial component in an amount effective to disinfect lens contacted with said solution, the antimicrobial component comprising of a primary, secondary, or tertiary alkyl having the following formula

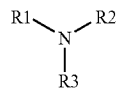

where R1 is a $C_{13-17}$ alkylamine, and R2 and R3 are each independently H or —$CH_3$;
   taurine in an amount effective to protect ocular tissue cell membranes;
   a non-ionic surfactant in an amount effective in cleaning a contact lens contacted with said solution;
   a buffer component in an amount effective in maintaining the pH of said solution within a physiologically acceptable range;
   a viscosity inducing component selected from the group consisting of cellulosic derivatives and mixtures thereof in the range of about 0.05% to about 5.0% w/v) of the total solution;
   a chelating component in an amount less than 0.05% (w/v) of the total solution; and
   a tonicity component in an amount effective in providing the desired tonicity to said solution.

6. A process for mitigating ocular tissue insult comprising:
   admininstering an aqueous liquid medium to a user's eye, the aqueous liquid medium comprising:
   a first antimicrobial component in an amount effective to disinfect a contact lens contacted with said solution, the antimicrobial component comprising; primary, secondary, or tertiary alkylamine having the following formula

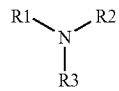

where R1 is a C13-17 alkyl, and R2 and R3 are each independently H or —CH3;
   taurine in an amount effective to protect ocular tissue cell membranes; and
   a non-ionic surfactant in an amount effective in cleaning a contact lens contacted with said solution.

7. The process of claim 6, wherein the alkylamine is selected from the group consisting of myristylamine and cetylamine.

8. The process of claim 6, wherein administering step is conducted so that the aqueous liquid medium is temporarily emplaced in the user's eye.

9. The process of claim 6, wherein administering step is conducted so that the uptake of the aqueous liquid medium into at least one of a soft-contact lens and a rigid gas permeable tens is achieved.

10. The process of claim 6, wherein the aqueous liquid medium further comprises a second antimicrobial component.

* * * * *